United States Patent
Weisenberger et al.

(10) Patent No.: US 9,217,744 B1
(45) Date of Patent: Dec. 22, 2015

(54) METHOD AND APPARATUS TO IMAGE BIOLOGICAL INTERACTIONS IN PLANTS

(71) Applicant: JEFFERSON SCIENCE ASSOCIATES, LLC, Newport News, VA (US)

(72) Inventors: Andrew Weisenberger, Yorktown, VA (US); Gregory M. Bonito, Durham, NC (US); Chantal D. Reid, Durham, NC (US); Mark Frederick Smith, Catonsville, MD (US)

(73) Assignee: JEFFERSON SCIENCE ASSOCIATES, LLC, Newport News, VA (US)

( * ) Notice: Subject to any disclaimer, the term of this patent is extended or adjusted under 35 U.S.C. 154(b) by 31 days.

(21) Appl. No.: 13/970,314

(22) Filed: Aug. 19, 2013

(51) Int. Cl.
*G01N 33/53* (2006.01)
*G01N 33/569* (2006.01)
*G06T 7/00* (2006.01)

(52) U.S. Cl.
CPC .......... *G01N 33/56961* (2013.01); *G06T 7/004* (2013.01)

(58) Field of Classification Search
CPC ................................................ G01N 2333/415
USPC ......................................................... 250/362
See application file for complete search history.

(56) References Cited

PUBLICATIONS

Kanno et al.,"Development of real-time radioisotope imaging systems for plant nutrient uptake studies", Philisophical Transactions of The Royal Society, Phil. Trans. R. Soc. B (2012) 367, 1501-1508 doi:10.1098/rstb.2011.0229.*

* cited by examiner

*Primary Examiner* — Marcus Taningco

(57) ABSTRACT

A method to dynamically image the actual translocation of molecular compounds of interest in a plant root, root system, and rhizosphere without disturbing the root or the soil. The technique makes use of radioactive isotopes as tracers to label molecules of interest and to image their distribution in the plant and/or soil. The method allows for the study and imaging of various biological and biochemical interactions in the rhizosphere of a plant, including, but not limited to, mycorrhizal associations in such regions.

17 Claims, No Drawings

METHOD AND APPARATUS TO IMAGE BIOLOGICAL INTERACTIONS IN PLANTS

The United States of America may have certain rights to this invention under Management and Operating Contract No. DE-AC05-84ER 40150 from the Department of Energy.

FIELD OF THE INVENTION

The present invention relates to methods for imaging certain biological interactions and biochemical processes in plant life, and, more particularly, the use of radioisotope-labeled compounds to image processes and interactions within the roots and root systems of plants.

BACKGROUND OF THE INVENTION

As a component of any ecosystem, a plant's biochemical activity and life processes are frequently intertwined with the activity of a variety of microorganisms that live in close proximity to the plant, i.e. microbes that live in proximity to the plant's roots or root system. Microbes in the soil in this area are influenced by the root and, conversely, the root is influenced by the microbes. This area of plant/microorganism interaction within the soil is known as the rhizosphere.

In addition to acquiring material from their soil environment, plants frequently exude various compounds into the same environment. Chemical communication and interaction frequently occurs between plants and microbes. Indeed, plants exude substances which can attract various microbes or repel microbes. The chemical interaction between the roots and microbes can both directly and indirectly affect systemic plant physiology.

Plants require a variety of raw materials and essential nutrients which, excluding a select few elements, must be obtained from the soil in which the plant is located. Typically, the nutrient uptake is carried out by or through a plant's roots or root system. Two nutrients that are uniformly required by plants in fairly large quantities are Nitrogen and Phosphorus. Although not always required, the symbiotic assistance of fungi often enhances many plants' uptake of these and other essential nutrients.

For example, Nitrogen and Phosphorus uptake is frequently facilitated through an association between the plant and one of various species of fungi inhabiting the rhizosphere. In a mycorrhizal association, a microbe fungus colonizes the roots of a host plant thereby engaging in a symbiotic relationship which benefits both organisms. This is done either intracellularly, as with arbuscular mycorrhizal fungi which actually penetrate plant cell walls, or extracellularly, as with ectomycorrhizal fungi which wrap around the epidermal cells of roots.

Recently much attention in plant ecophysiology research has been focused on studying the biology of the rhizosphere and the mycorrhizal association. The difficulty, however, is that the current methodological approaches, by their very nature, are inherently destructive or cannot otherwise be carried out under natural field conditions. For instance, the vast majority of methods require the removal of the root system from the soil. Further, these approaches are generally difficult to apply to large numbers of plants comprising a larger ecosystem.

A method is therefore needed to quantify and image the biological interactions of plants and fungi, and more specifically, mycorrhizal associations, without disturbing the plant or soil so that longitudinal studies can be repeatedly performed on the same plant and soil/microbe biological system.

To date, no one has used radioisotope based techniques for examining the rhizosphere and, more specifically, mycorrhizal associations in the rhizosphere.

OBJECT OF THE INVENTION

It is an object of the invention to provide a novel method for imaging certain biological interactions and biochemical processes in plants.

It is a further object of the invention to provide a specific imaging method for the observation of plant-fungal interactions and mycorrhizal associations without disturbing the plant or soil.

SUMMARY OF THE INVENTION

The present disclosure provides a method to dynamically image the actual translocation of molecular compounds of interest without disturbing the plant's root or the soil in which the root is embedded. The technique makes use of radioactive isotopes as tracers to label molecules of interest and to image their distribution in the plant and/or soil.

More specifically, one embodiment of the invention can be used to visualize mycorrhizal interactions. A radioactive tracer is used to tag or label a microbial or root based molecule such as chitin, which is typically found in the cell walls of fungi. The tracer is introduced into the soil and subsequently binds with, or is incorporated into, the fungi in the soil. A radioisotope imaging detector is then used to determine the distribution of the radioisotope labeled molecule. Software algorithms may be used to further refine the processing, reconstruction, and display of the image or images showing the radioisotope distribution.

DETAILED DESCRIPTION

The instant invention discloses a novel method to dynamically image the actual translocation of molecular compounds of interest without disturbing a plant's root(s) or the soil in which the root is embedded. This technique makes use of radioactive isotopes as tracers to label molecules of interest and to image their distribution in the plant and/or soil.

Two classes of radioisotopes, single photon emitters and β emitters (positrons and electrons), have been used in plant research as well as in biomedical settings. Radioisotopes that are single photon emitters emit a single γ-ray or x-ray (high energy photon) during decay while positron emitters emit a β-particle (positron), the anti-particle of an electron. The positron, depending on its kinetic energy, travels a very short distance (e.g., 1-2 mm in water) before encountering an electron, which leads to positron-electron annihilation that in turn produces two 511 keV photons, which travel away from the interaction point in opposite directions. Radioisotope imaging is achieved by using autoradiography for the β emitters, single photon emission computed tomography (SPECT) for single photon emitters, and positron emission tomography (PET) for positron emitters.

Labeling techniques that use short-lived radioisotopes provide a range of appropriate temporal and spatial scales to directly address different sets of questions concerning plant functions and biochemical mechanisms. Depending on the physiological process and radioisotope involved, different imaging modalities are needed. For example, a SPECT imaging system with a field of view and spatial resolution suitable for plant research would create opportunities to study plants over several days. This greatly extends the typically shorter response time measurements, usually, less than 12 hours, made using PET systems. In addition, SPECT systems allow for the study of important minerals tagged with radioisotopes that are not accessible with PET, e.g., $^{43}$K ($t_{1/2}$=22.3 hours, 373 keV & 617 keV), which enables measurements relevant to understanding regulatory networks that control enzyme regulation, ionic transport that regulate the opening and closing of the stomata, mineral uptake and transport and, consequently, plant growth and production.

As mentioned, PET imaging has physical limits of achievable spatial resolution defined by the range of the positron in the specimen or object under study before positron-electron annihilation. Furthermore, when production of the 511 keV gamma ray pair occurs in low Z and low-density materials, particularly in the form of a flat object such as a plant leaf, the positron range can become even more of a problem, since in thin leaves of plants there is an elevated probability that the positron may escape the plant without undergoing an annihilation, an uncommon occurrence for positron emission within animals and humans. In contrast, there is no such limit in single gamma imaging, and very high spatial resolution (<1.0 mm FWHM) can be achieved, providing proper collimation systems are used for the energy of interest.

Direct detection of β particles (positrons: β+ and electrons: β−) is another radioisotope detection method. Autoradiographic film or phosphor imaging plates have been used for β particle imaging (such as emitted from the $^{32}$P-β particle and $^{11}$C positron) and high resolution images of thin objects such as leaves may be obtained. However, this imaging procedure using commercially available technology requires the plant be placed in a dark box. Thus, the technique is limited to static images or short-term processes that occur in the dark. Natural daytime physiological processes that require light cannot be done using this technique. In addition, such imaging is commonly done on a harvested plant preventing longitudinal study of the same plant over an extended period of time.

These non-invasive radioisotope methods set forth herein can play an important role in studying the processes responsible for particular plant responses in changing environmental conditions. Plant physiological research has focused on the complexity of chemical plant signal molecules, such as sugars, peptides, proteins and hormones, in response to environmental changes.

One use of an embodiment of the present invention would provide a method to visualize microbial/root interaction (e.g., mycorrhizal association). Molecules tagged with the radioisotope are introduced into the plant via natural uptake pathways. This uptake occurs in natural soil as well as in other media, such as in hydroponic growth situations.

In hydroponics, plants are grown bathing in a mineral nutrient solution without soil and tagged organic molecules of interest, such as glucose or amino acid, can be applied via roots. For nutrients normally encountered in the soil, the growth of plants in hydroponic solutions facilitates the addition of tracer molecules that are taken up by the roots and transported where needed in the plant. However, as mentioned, such tagging could also be done in natural soils, a critical distinction of the instant method versus existing techniques.

The imaging method provided herein can be used when the root or root system of a plant is situated in a container or enclosure, housing hydroponic solution, soil, or any similar material, which allows the placement of one or more imaging devices around its perimeter. It would also be possible to place certain imaging devices around a plant root or root system in field conditions which would obviate the need for an enclosure or container.

A radioactive tracer and a tag are selected. The tag is a molecule or substance chosen for its ability to bind with a particular microbial or root-based target molecule such as (but not limited to), the chitin of a fungus or amino acid exuded by the roots. Chitin is a protein typically found in the cell wall of fungus but not in plants.

Once the tag is selected, a suitable radioactive tracer must be associated with the tag. The radioactive tracer must emit sufficiently high energy photons (x-rays or gamma-rays) capable of passing through the soil and container (when a container is used). Tracers such as, but not limited to, Iodine-125, Iodine-123, Carbon-11, or Technetium-99m can be used. It will be noted that while preferred embodiments may incorporate the foregoing tracers, any radioactive tracer possessing suitable characteristics may be used.

The tagged molecule is then introduced into the soil or hydroponic solution. The tagged molecule further binds to a target or is directly incorporated into the fungal or plant structure. The soil is then washed. Washing can be accomplished by passing a sufficient amount of water into or through the soil so as to wash away or eliminate the tagged molecules that do not affix themselves or bind to a target. This washing step is not found in any conventional human medical radioisotope imaging techniques.

Following washing, the remaining tagged molecules are imaged using isotope detection techniques, such as imaging with a radioisotope imaging detector, e.g., a crystal scintillator or solid-state based gamma camera used in SPECT imaging or PET imaging. Computer algorithms are used to reconstruct images from radioisotope imaging detectors to allow the determination of the distribution of the radioisotope labeled molecule. Among other benefits, the computer algorithms can assist by making different types of attenuation corrections based upon soil characteristics.

Imaging the target with a detector external to the container or pot allows an observer to actually image a plant root or root system in its natural environment. One is therefore able to locate the fungus and to see where the fungus grows and how active the fungus is. No destruction of soil or root structures is required and, as a result, the experiment can be repeated on the same plant, under substantially similar conditions, over time. Further, unlike other known methods using optical tracers, the instant method does not require direct unobstructed visual observation.

The above described embodiment using a chitin binding material, or any similar tagging material, can be used to quantify and image the biological interaction of mycorrhizal association without disturbing the plant or soil so that longitudinal studies can occur on the same plant and soil/microbe biological system. Indeed, in cases where a particular fungus of interest has attached itself to the exterior perimeter of a root, extensive images of the root outline itself can be generated over time.

In cases where additional information is required, another imaging modality, such as X-ray CT or MRI, may be applied in conjunction with the instant method in order to determine the physical location of the roots. This additional imaging information may then be overlaid on the image generated by the instant radioisotope imaging method set forth above. The in vivo molecular imaging techniques disclosed herein may be used to further the study of physiological interaction at the root/soil/microbe interface. Advances in the understanding of these aspects of plant physiology may lead to many breakthroughs, including new advances in food production, environmental remediation and bio-fuels.

While the invention has been described in reference to certain preferred embodiments, it will be readily apparent to one of ordinary skill in the art that certain modifications or variations may be made to the system without departing from the scope of the invention claimed below and described in the foregoing specification.

What is claimed is:

1. A method of imaging the translocation of molecular compounds of interest in the root system and the rhizosphere of a plant, comprising:
   Providing a plant with a root or root system for study;
   Providing a compound or molecule which will bind to a target;
   Labeling said compound or molecule with a radioisotope;
   Tagging the target with the labeled compound or molecule;
   Removing excess labeled compound or molecule;
   Providing a radioisotope imaging detector and imaging algorithms; and,
   Imaging the emissions from the labeled compound or molecule within said
   root or root system using said radioisotope imaging detector and imaging algorithms.

2. The method of claim 1 wherein said radioisotope imaging detector is a crystal scintillator.

3. The method of claim 2 wherein said radioisotope imaging detector is a solid-state based gamma camera.

4. The method of claim 1 wherein said target is a molecule or compound exuded by said plant root or root system.

5. The method of claim 1 wherein said target is a fungus.

6. The method of claim 5 wherein said target is a component of the cell wall of a fungus.

7. The method of claim 6 wherein said component is chitin.

8. The method of claim 1 further comprising providing said plant in soil wherein said removing excess labeled compound or molecule consists of washing the soil with water or equivalent liquid.

9. The method of claim 1 wherein said tagging the target comprises introducing the labeled compound or molecule in to soil surrounding the root or root system.

10. The method of claim 1 wherein said radioisotope is selected from the group of Iodine-125, Iodine-123, or Carbon-11.

11. A method of studying activity in the rhizosphere, comprising:
   placing a plant under study in which the plant root system is positioned in a container of hydroponic solution or soil or similar material that allows the placement of imaging devices about its perimeter;
   selecting a radioactive tracer which emits high energy photons capable of passing through the soil and container;
   applying said radioactive tracer to tag or label a microbial or root based molecule;
   introducing the tagged molecule into the soil or hydroponic solution;
   imaging said radioactive tracers using a radioisotope imaging detector; and
   using computer algorithms to reconstruct images from said radioisotope imaging detectors thereby allowing the determination of the distribution of the radioisotope-labeled molecule.

12. The method of claim 11 wherein said radioisotope imaging detector is a crystal scintillator.

13. The method of claim 11 wherein said radioisotope imaging detector is a solid-state based gamma camera.

14. The method of claim 11 wherein said radioactive tracer is selected from the group of Iodine-125, Iodine-123, Carbon-11, or Technetium-99m.

15. A method of imaging mycorrhizal association in the root system and the rhizosphere of a plant, comprising:
   Providing a plant with a root or root system for study;
   Identifying a compound or molecule which will bind to a particular target associated with a fungus or fungal growth;
   Labeling said compound or molecule with a radioisotope so as to form a tracer complex;
   Binding the tracer complex to the target;
   Removing excess tracer complex;
   Providing a radioisotope imaging detector and imaging algorithms; and,
   Imaging the emissions from said tracer complex within said
   root or root system using said radioisotope imaging detector and imaging algorithms.

16. The method of claim 15 wherein said compound or molecule is such that it will only bind to a target in a specific species of fungus.

17. The method of claim 15 wherein the method of imaging serves to provide a quantitative assessment of the biochemical interaction between the fungus and the plant.

* * * * *